US012674749B2

(12) United States Patent
Myrick et al.

(10) Patent No.: US 12,674,749 B2
(45) Date of Patent: Jul. 7, 2026

(54) SPECTROSCOPY COMBINING BASE STATIONS AND UNMANNED AERIAL VEHICLES

(71) Applicant: University of South Carolina, Columbia, SC (US)

(72) Inventors: Michael L. Myrick, Columbia, SC (US); Nikolaos Vitzilaios, Lexington, SC (US); Michael Hodgson, Columbia, SC (US); Bruce A. Davis, Oxford, MS (US)

(73) Assignee: University of South Carolina, Columbia, SC (US)

( * ) Notice: Subject to any disclaimer, the term of this patent is extended or adjusted under 35 U.S.C. 154(b) by 119 days.

(21) Appl. No.: 18/118,386

(22) Filed: Mar. 7, 2023

(65) Prior Publication Data

US 2023/0280270 A1 Sep. 7, 2023

Related U.S. Application Data

(60) Provisional application No. 63/317,171, filed on Mar. 7, 2022.

(51) Int. Cl.
| | |
|---|---|
| *G01N 21/39* | (2006.01) |
| *B64U 10/80* | (2023.01) |
| *B64U 101/00* | (2023.01) |
| *G01N 33/00* | (2006.01) |

(52) U.S. Cl.
CPC ............. *G01N 21/39* (2013.01); *B64U 10/80* (2023.01); *G01N 33/0027* (2013.01); *B64U*

*2101/00* (2023.01); *G01N 2201/0214* (2013.01); *G01N 2201/06113* (2013.01)

(58) Field of Classification Search
CPC ............... G01N 21/39; G01N 33/0027; G01N 2201/0214; G01N 2201/06113; G01N 2021/1795; G01N 2021/399; B64U 10/80; B64U 2101/00
See application file for complete search history.

(56) References Cited

U.S. PATENT DOCUMENTS

| | | | | |
|---|---|---|---|---|
| 6,727,849 | B1 * | 4/2004 | Kirk | G01S 19/44 |
| | | | | 342/464 |
| 11,860,688 | B1 * | 1/2024 | Paczkowski | G06F 16/27 |
| 2002/0169557 | A1 * | 11/2002 | Gilbert | G01N 33/0004 |
| | | | | 702/3 |
| 2013/0176570 | A1 * | 7/2013 | Beck | G01N 21/314 |
| | | | | 356/432 |
| 2014/0350886 | A1 * | 11/2014 | Metzler | G01S 7/003 |
| | | | | 702/150 |

(Continued)

*Primary Examiner* — Thanh Luu
*Assistant Examiner* — Mai Thi Ngoc Tran
(74) *Attorney, Agent, or Firm* — Douglas L. Lineberry

(57) ABSTRACT

A spectroscopy system including a base station having a reflecting telescope and a laser light source coupled to the telescope, the laser providing an outgoing light signal; at least one Unmanned Aerial Vehicle containing a mobile retroreflector configured to receive the light signal from the laser and return a light signal back to the telescope; a detector to record the intensity of the returning light signal; and optical components for spectroscopic measurements, the optical components utilizing the intensity of the returning light signal, revealing the presence of a chosen narrow band for the purpose of detecting a target.

16 Claims, 12 Drawing Sheets

(56) References Cited

U.S. PATENT DOCUMENTS

| | | | | |
|---|---|---|---|---|
| 2016/0334507 | A1* | 11/2016 | Hangauer | G01J 3/0278 |
| 2017/0336281 | A1* | 11/2017 | Waxman | G01N 21/359 |
| 2018/0172809 | A1* | 6/2018 | Efimov | H04L 27/144 |
| 2019/0265123 | A1* | 8/2019 | Rieker | G01N 33/0062 |
| 2021/0190493 | A1* | 6/2021 | Yuasa | G01C 15/002 |
| 2022/0136818 | A1* | 5/2022 | Righetti | G01B 9/02087 |
| | | | | 356/497 |

* cited by examiner

1

SPECTROSCOPY COMBINING BASE STATIONS AND UNMANNED AERIAL VEHICLES

CROSS-REFERENCE TO RELATED APPLICATION

This application is claims benefit of U.S. Provisional Patent Application No. 63/317,171, filed on Mar. 7, 2022, which is incorporated herein by reference in its entirety.

FIELD OF THE INVENTION

The present disclosure relates to spectroscopy and more particularly to a method and system for obtaining line-of-sight and remote optical measurements of a target using a base station and a remote station.

2) DESCRIPTION OF RELATED ART

The potential for toxic atmospheric releases is a world problem. Source term characterization and accurate ATD models are effective tools to protect human health and environmental resources during release events. While ATD models like HYSPLIT are very sophisticated the source term information is sometimes not. Better parameterization of HYSPLIT would improve the modeled prediction of plume transport and emergency response. Research to improve model predictions benefit from accurate validation methods.

Existing technologies exist in the field of spectroscopy systems, yet these systems and their components have not yet been combined in the fashion of the present disclosure. For example, light sources (e.g., lasers, LEDs, lamps, and others as a person skilled in the art would recognize) and detectors (photodiodes, photomultipliers, avalanche photodiodes, single-photon-counting apparatus, and others as a person skilled in the art would recognize), retroreflectors (corner cube, Cat's eye, Luneburg lenses, or other devices as a person skilled in the art would recognize), telescopes (reflecting, refracting, and other related light-gathering optics as a person skilled in the art would recognize), atmospheric modeling software, exposure software, etc. are all demonstrated technologies. Related technologies, such as Light Detection and Ranging (LiDAR) systems, exist, and are primarily used for terrestrial applications. Unmanned Aircraft Systems (UAS) are mostly used for visual based inspections. Other applications that require specialized sensors are limited by the payload and flight time of the current systems. There are existing, commercially available Unmanned Arial Vehicle (UAV)-based systems for conducting air quality sampling that rely on sensors mounted on the UAV. Measurements of atmospheric parameters using a fixed sensor on a UAV (e.g., temperature, humidity, wind velocity) exist. Geolocational technologies, such as Global Navigation Satellite System (GNSS) also exist. Measurements of gases, liquids and solids using optical spectroscopy are well-known. Note that throughout this disclosure, the terms "UAV" and "sUAS" shall be used interchangeably.

However, these existing technologies have not yet been combined in such a fashion as described herein. Further, the system described herein is for measurement of the absorption or emission of light by chemical or physical means as a method for sensing the presence of a chemical or physical condition.

SUMMARY OF THE INVENTION

In one aspect of the present disclosure, a spectroscopy system is provided. The spectroscopy system includes a base station having a reflecting telescope and a laser light source coupled to the telescope, the laser providing an outgoing light signal. A mobile retroreflector receives the light signal from the laser and returns a light signal back to the telescope. A detector records the intensity of the returning light signal. The system also includes optical components for spectroscopic measurements, the optical components utilizing the intensity of the returning light signal, revealing the presence of a chosen narrow band for the purpose of detecting a target.

The disclosed proposed methods and systems will map the geographic extent and trajectory, including rate of dispersion, of an atmospheric release in near-real time providing both regulatory and industry officials rapid access to critical information on which to initiate mitigation response and public health advisory messaging. The mobility of a UAV makes it possible to quickly reach a site and map gases in response to an event, or to patrol a regular line. The use of a base station eliminates the need to restrict the size, weight and power of the system because the laser and power sources are not carried by the UAV itself. The use of a base station and UAVs permits the proposed methods and systems to perform multiple tasks by changing the wavelength, resolution, pulse rate, etc., of the source without consideration of physical and electrical constraints. The use of a base station allows for rapid switching between multiple remote stations—either on UAVs or fixed reference sites. The use of the UAV as a remote station also allows for on-the-spot measurements of wind conditions. The UAV can also be pre-positioned and launched autonomously for data collection along pre-defined routes for routine monitoring.

The system disclosed herein rapidly detects a wide variety of toxic chemicals and maps the dispersion of those chemicals in three dimensions. In certain embodiments, the system disclosed herein includes lasers coupled with a flexible drone-mounted retroreflector target or detector/transponder combination to detect and map atmospheric releases. In certain embodiments, the system can be installed as a fixed system at a facility or mounted in a mobile response vehicle for rapid response to any location within the jurisdiction of responsibility. The system disclosed herein can be scaled to fit any monitoring application. In certain embodiments, the output from the system will be available in real-time to NOAA WFOs as well as the HYSPLIT modeling team for improved incident response products.

In one aspect of the disclosure, a spectroscopy system is provided. The spectroscopy system includes a base station includes a reflecting telescope and a laser light source coupled to the telescope, the laser providing an outgoing light signal; a detector to record intensity of a returning light signal; and optical components for spectroscopic measurements, the optical components utilizing the intensity of the returning light signal, revealing the presence of a chosen narrow band for the purpose of detecting a target; and at least one Unmanned Aerial Vehicle (UAV) containing a mobile retroreflector configured to receive the light signal from the laser and return the light signal back to the telescope.

In one embodiment of this aspect, the laser light source is a quantum cascade laser (QCL). In another embodiment, the detector is configured to sweep the returning light signal in wavelength to reveal the presence of the chosen narrow band to detect a target compound in the atmosphere. In another embodiment, the base station further comprises at least one actuator to allow the telescope to track a path of the mobile retroreflector. In another embodiment, the base station is fixed. In another embodiment, the base station is mobile. In another embodiment, the base station is at least one of ground-based, water-based, or air-based.

In another embodiment, the detected target is one or more gases. In another embodiment, the detector and the optical components are located in the base station. In another embodiment, the system further includes at least one of a beacon and a fiduciary mark located on or near the at least one mobile retroreflector, wherein the telescope is configured to track the at least one mobile retroreflector by following the beacon or fiduciary mark. In another embodiment, the telescope is configure to track the at least one mobile retroreflector by using a Global Navigation Satellite System (GNSS) Real Time Kinematic (RTK)-derived position/heading broadcast received from the at least one mobile retroreflector.

In another embodiment, the system further includes a control station coupled to the telescope, the control station configured to direct the at least one mobile retroreflector and the telescope in order to coordinate tracking of the at least one mobile retroreflector by the telescope. In another embodiment, the UAV has a preprogrammed circular flight path. In another embodiment, the system further includes fixed retroreflector stations near known potential sources. In another embodiment, the UAV further includes one or more mirrors, refractive optics, reflective optics, dispersive optics, and prism device. In another embodiment, the base station and components therein are configured for at least one of terrestrial vapor monitoring, stack gas measurement, area survey, leak detection, and planetary science.

BRIEF DESCRIPTION OF THE DRAWINGS

The construction designed to carry out the system of the present disclosure will hereinafter be described, together with other features thereof. The present disclosure will be more readily understood from a reading of the following specification and by reference to the accompanying drawings forming a part thereof, wherein an example of the present disclosure is shown.

Figure 1:
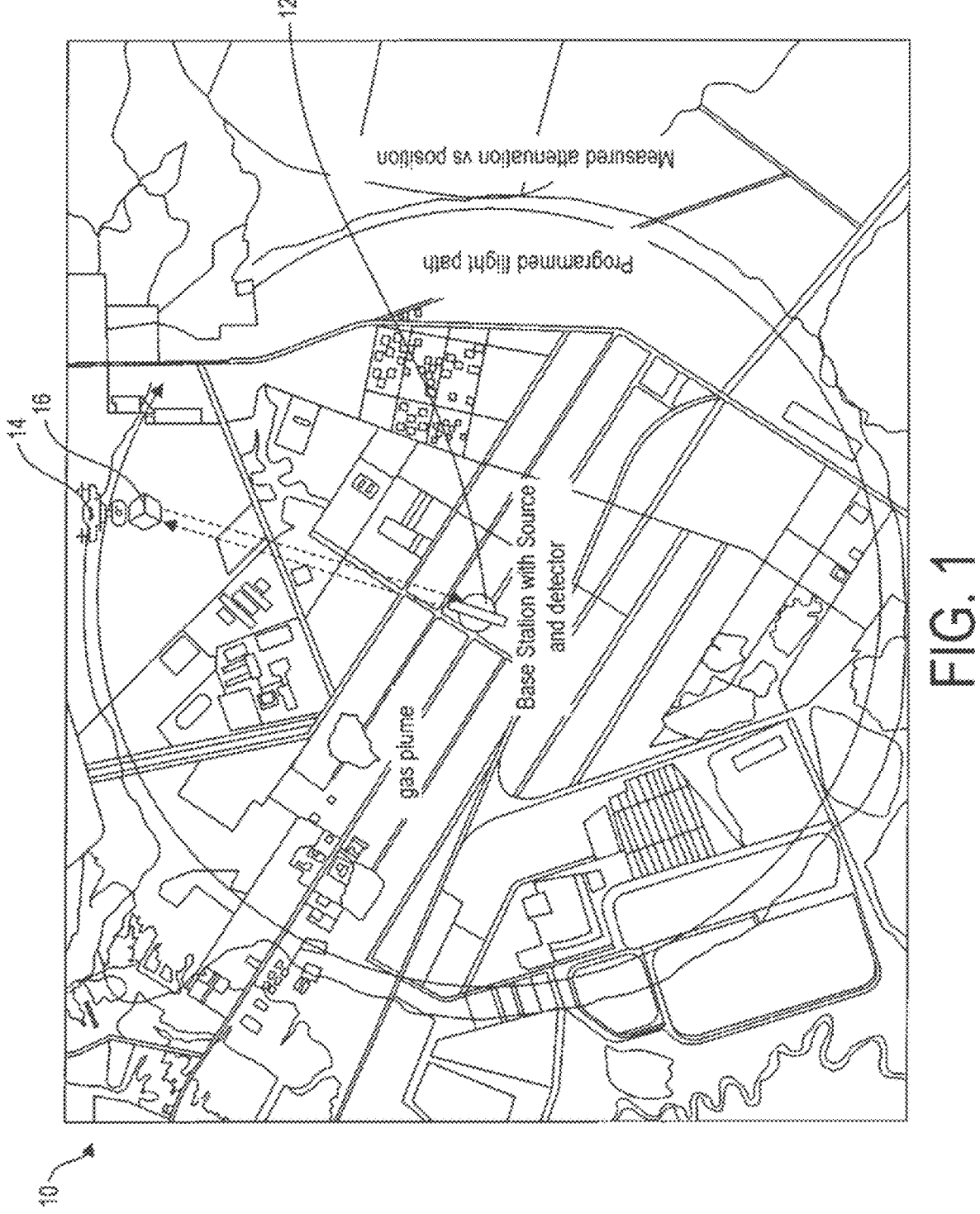
FIG. 1 illustrates an aerial view of a spectroscopy system including a base station and mobile retroreflector exchanging light signals in accordance with embodiments of the methods and systems disclosed herein.

It will be understood by those skilled in the art that one or more aspects of this invention can meet certain objectives, while one or more other aspects can meet certain other objectives. Each objective may not apply equally, in all its respects, to every aspect of this invention. As such, the preceding objects can be viewed in the alternative with respect to any one aspect of this invention. These and other objects and features of the invention will become more fully apparent when the following detailed description is read in conjunction with the accompanying figure and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

DETAILED DESCRIPTION OF A PREFERRED EMBODIMENT

With reference to the drawings, the invention will now be described in more detail. Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are herein described.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

In view of the apparatuses and methods further disclosed herein, exemplary embodiments may be implemented in such fields as stack gas emissions monitoring; fence-line monitoring; measurement of accidental or intentional releases; modeling of exposure; measurement of diffuse vapor emissions from underground sources; planetary atmospheric sciences; and national defense monitoring applications. The approaches can be used for real-time incidences or for data collection when calibrating atmospheric release models.

Further applications of the present disclosure include industrial applications that either require atmospheric monitoring or benefit from atmospheric monitoring through the mitigation of impact from accidental releases. Operations where venting of gases occur on a regular basis such as petrochemical facilities, manufacturing operations, or waste disposal facilities are applications for the methods and systems disclosed herein, as well as emergency response operations at federal, state, local, or tribal levels are markets for this technology to insure the safety of response personnel. Military operations where the security of personnel is an issue are also applications for the methods and systems disclosed herein in order to monitor their theater of operations for hazardous materials. Further, the environmental monitoring services industry which currently use passive technologies or which do not have that system capabilities expressed in the present disclosure and who want to expand their service offering are also an application of the methods and systems of the present disclosure.

Existing products to monitor atmospheric constituents consist of stationary passive samplers, FTIR scanners, and UAV-based passive samplers. All these products do not have the ability to accurately measure the three-dimensional extent of an atmospheric chemical that the methods and systems disclosed herein will have. The quantum cascade laser (QCL) instrument, which is one of many lasers that can be used with the disclosed invention, is fundamentally different than FTIR instruments used in some applications with the QCL instrument having a much greater signal to noise ratio and a higher resolution.

In one embodiment, the disclosed system is a laser/drone system for detecting and tracking atmospheric releases with reports sent to identified locations. The system includes stationary targets/transponders for persistent observation and alerting for deployment of drones for tracking and mapping. In certain embodiments, the system includes instrumenting selected emergency response/law enforcement vehicles to serve as persistent mobile monitoring stations. In further embodiments, the system incorporates critical infrastructure and population density data with the mapping and tracking of hazardous atmospheric releases in a GIS compatible with the situational awareness dashboard of emergency response. The system could then report on the track of a plume and potential impact to CI and public health.

Referring to FIG. 1, which is not intended to limit the use or application or variations of the system, one exemplary use of the spectroscopy system 10 of the present disclosure for one particular application, i.e., patrolling for gas plumes, is shown. The system 10 as shown consists of a base station 12, which in one embodiment includes a reflecting telescope and laser light source such as a quantum cascade laser producing, for example, 50 mW of laser light in the mid-infrared spectral window (telescope and laser light source not shown in FIG. 1). The laser light source is coupled to the reflecting telescope so that an outgoing light signal bounces from a main mirror of the reflecting telescope and is directed toward at least one UAV 14 having a mobile retroreflector 16, or, in another embodiment reflects from a small added mirror in the reflecting telescope toward the mobile retroreflector 16, or, in another embodiment, is directed by being mounted on the tube of the reflecting telescope, or, in yet another embodiment, is mounted on the back of a secondary mirror of the reflecting telescope. If projected by the telescope, the focus of the laser on the retroreflector 16 can be actively controlled by the GNSS-derived distance between the base station 12 and the mobile retroreflector 16.

In one embodiment, the position of base station 12 is determined prior to flight using survey-grade GNSS measurements, such as Real-Time Kinematic (RTK) or Post Processed Kinematic (PPK). The position of UAV 14 is precisely determined in real-time using GNSS RTK and propagated in the next second using heading and trajectory (e.g., through two GNSS receivers or an Inertial Navigation System (INS) of the UAV). Additional fine-tuning of the orientation of the telescope can be made by optical image correlation if needed, and adjustments for atmospheric distortion can be made via adaptive optics solutions if desired. Position correction signals can be generated by each of these approaches if desired to refine the GNSS-based aiming of the telescope at the mobile retroreflector 16.

The laser wavelength or range of wavelengths can be configured for the application. In the present disclosure, the non-limiting application is for the measurement of a single gas using a small range of infrared wavelengths from a mid-infrared laser based on infrared vibration-rotation spectroscopy. This example is not intended to limit the modes of measurement or the wavelength(s) of measurement to which the present disclosure may be applied.

The limit of detection (LOD) for hydrocarbons using Fourier-transform infrared (FTIR) spectroscopy in fenceline monitoring has been reported to be in the sub-10-ppb range, while the LOD for Ultra Violet (UV) absorption by aromatic organic vapors is reported to be below 1 ppb. The LOD for $CO_2$ releases by the same method are of the order ~10 ppm. These values are for 60-second-long measurements from the report "Demonstration of Remote Sensing Fenceline Monitoring Methods at Oil Refineries and Ports", http://www.aqmd.gov/docs/default-source/fenceline_monitroing/earlier_fenceline_studies/ucla_fenceline_monitroing_technology_study_2012-2014.pdf prepared by faculty of the Department of Atmospheric and Oceanic Sciences at UCLA in January 2015. Note that FTIR sources are of low brightness and low collimation compared to quantum cascade and similar tunable lasers, and FTIRs typically provide low spectral resolution compared to the rotational fine-structure lines of the infrared bands of gases, meaning that better LODs and faster measurements are likely with the proposed system than with an FTIR. LODs for gases that have not been previously determined can be estimated from high resolution quantitative spectroscopy of the gases reported in the technical literature and databases.

As shown in the spectroscopy system 10 of FIG. 1, UAV 14, containing one or more retroreflectors moves above a city landscape (the use of a city landscape in FIG. 1 is non-limiting, and one or more UAVs 14 can move above any geographic area, whether over land or sea. The intended path of UAV 14 is shown as a circle, while the actual path of UAV 14 is represented by the uneven line. Base station 12 is shown, and in one embodiment (discussed below) includes a detector. As further discussed below, light signals form base station 12 are transmitted to the one or more UAVs 14, where they contact one or more retroreflectors 16 therein, and return light signals from the retroreflectors 16 are transmitted back to base station 12.

Figure 2:
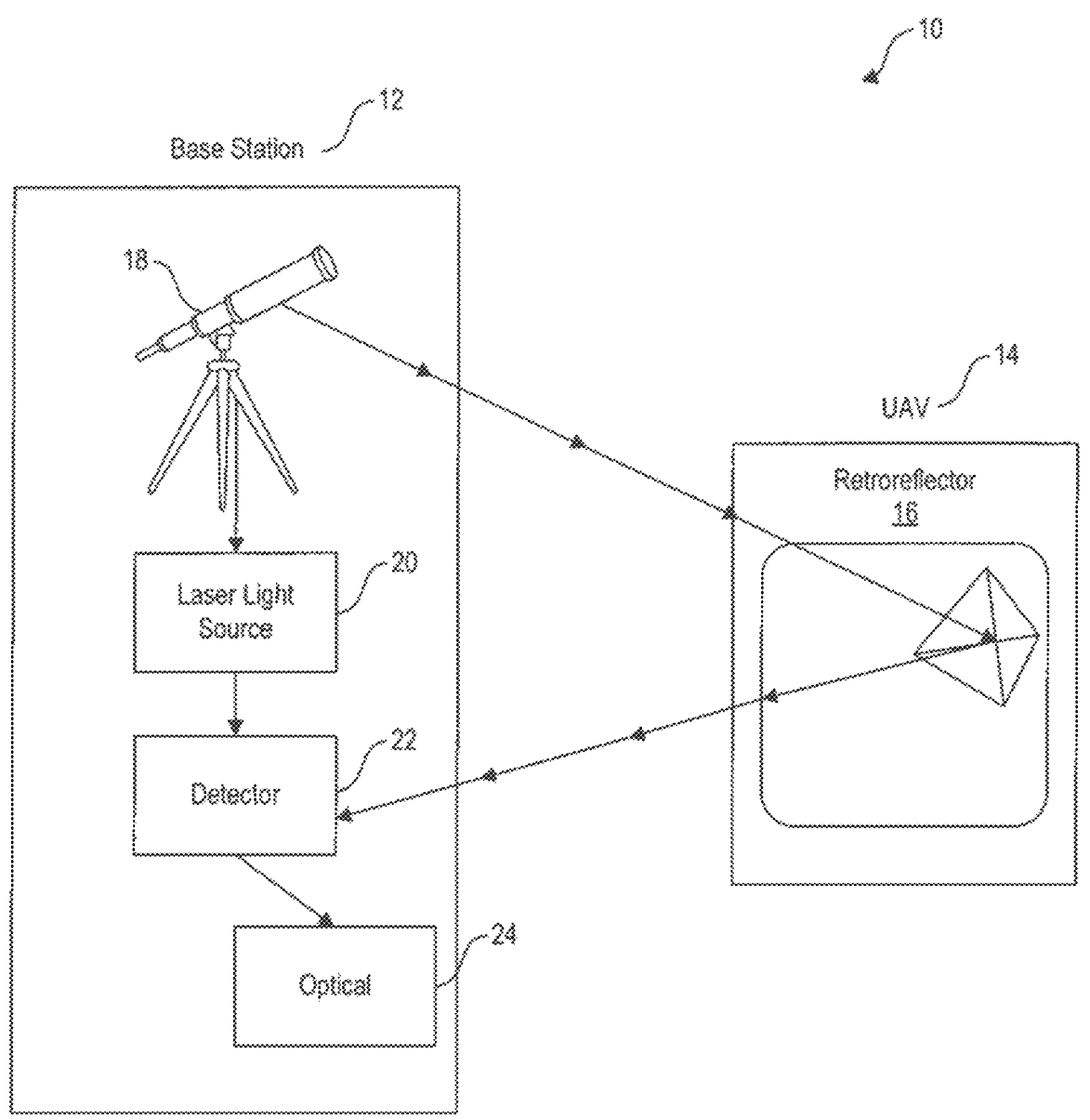
FIG. 2 illustrates the components of the base station of the spectroscopy system in accordance with embodiments of the methods and systems disclosed herein.

FIG. 2 illustrates, in one embodiment, base station 12, UAV 14, and the components therein. In one embodiment, base station 12 includes a reflection telescope 18, a laser light source 20, a detector 22, and optical components 24.

In one embodiment, the pointing of reflection telescope 18 is achieved by actuators that are computer-driven to track the mobile retroreflector 16. The tracking may be based either on following a beacon (radio, microwave, optical, etc.) or fiduciary mark located on or near the mobile retroreflector 16, or by using a precise GNSS RTK-derived position/heading broadcast from the UAV 14 back to the base station 12. The telescope 18 can track the mobile retroreflector 16 by following the beacon/mark or GNSS RTK-derived position, or can anticipate the trajectory of the mobile retroreflector's known flight plan to minimize error correcting, or can be coupled to a control station (shown in FIG. 3) that directs both the mobile retroreflector 16 and the telescope 18.

The beam projected by or from the telescope 18 illuminates the retroreflector 16, and the beam is thereby returned to the telescope 18. The returning light is separated from the exciting light by use of a beamsplitter, or without a beamsplitter if the beam was directed using a small added mirror that blocks direct view of the excitation inside the telescope optics. The returning light signal is directed to detector 22 where the intensity of the returning light signal is recorded. In one embodiment, an adaptive optics system can be used to compensate for atmospheric distortion at great distances. This could be enhanced using a second laser whose retroreflection serves the sole purpose of a guide star for the adaptive optics system, and whose wavelength can be chosen for convenience.

Included herein are embodiments in which polarization-rotating optics or coatings on the retroreflector 16 are used to permit polarized laser excitation to be separated more efficiently from the returning light from the retroreflector 16 by use of a polarizing beam splitter or other polarization sensitive optics.

Adaptive optical approaches can be used for detection, but can also be used to correct the exciting laser so that it strikes the retroreflector 16 despite atmospheric distortion. The returning light is coupled from the telescope using common optics to reach a detector 22 suitable for the main laser wavelength or wavelength range. If a rapidly tunable laser, or a pulsed laser, is used for the main laser, and if the time-response of the detector 22 is pertinent to the measurement, then the frequency response of the detector 22 becomes important and must be engineered by common methods to be fast enough to follow the relevant signals. In the case of a QCL or similar device, the wavelength range can be selected to cover a single rotational line of a target species in the atmosphere, such as methane, HCl, or other vapors or gas. Note that the operation of this system for gas detection depends on the presence of unique light absorption by the gas to distinguish it from non-target gases, or on light absorption that can be deconvoluted from other gases by use of mathematical tools such as artificial neural networks, partial least squares, support vector machines, principal components regression, and other approaches obvious to those skilled in the art.

The returned light from the mobile retroreflector 16 reaches detector 22, whose size must at minimum be sufficient to detect all the possible return signals from the retroreflector 16 when properly centered on the detector 22. The noise-equivalent power of the detector 22, or other parameter that may be more appropriate to different types of detectors 22, under whatever frequency response conditions are employed, must be adequate for measuring the signal with a reasonable signal-to-noise, the specific limitations of which are dependent on the desired detection limit of the analyte and the strength of the transition being probed, as well as the presence of any interfering chemical species and the temperature whenever the population of initial spectroscopic states can vary with temperature in a meaningful way. Atmospheric pressure can also vary the width and hence the apparent maximum strength of a transition, but these latter factors may be unimportant if the band is chosen well separated from other species and if the entire band shape is resolved.

In the case of a QCL, the wavelength is tunable in a couple of ways, including thermal tuning. The returning signal is therefore swept in wavelength and can reveal the presence of a chosen narrow band for the purpose of detecting the target compound in the atmosphere. Processing of the returned signal can be used to determine the absorption depth of a known line of a target compound, and thus the concentration of the target compound in appropriate units (such as ppm-meters for a single line of sight measurement).

The implementation shown in FIG. 1 gives the mobile retroreflector 16 a preprogrammed circular flight path, which might be appropriate if there is no available knowledge about the location of the atmospheric release. In this case, a gas plume would be detected by the absorption of laser light at the predetermined wavelength. The preprogrammed flight path gives only limited information on the plume. However, the UAV 14/mobile retroreflector 16 can return to the point at which the detection was made and approach the base station 12 to determine where the plume is located more exactly. A planned pattern of flight behind and through the plume can then be used to map out the concentration of the plume in space as an input to modeling software to determine exposure down-wind of the release. In the case where a release is known and an initial model run conducted, the target could be directed to the general location provided by facility managers or predicted model output and this system would be used to confirm the model predictions and track the trajectory of the plume in near-real time to coordinate a more effective response to the release.

The wind velocity in the area of the release can be determined by local meteorological data (e.g., COOP network), or by using ground-based stations for this purpose near the plume, an anemometer co-located with the base station, or by using GNSS-derived location and velocity measurements and wind sensors placed on the UAV, or by using the GNSS of the UAV coupled with control signals required for station-keeping or controlled motions of the mobile retroreflector 16. Each of these methods has advantages and disadvantages relative to one another, as will be apparent to one skilled in the art.

Together with the spatial data of a plume and wind velocity data, atmospheric modeling software can be used to predict downwind exposures and also to compute the amount of material released. When the atmospheric release point is not known, a footprint-modeling solution could be used to hindcast the likely origin of the release point.

The present disclosure provides, in one embodiment, a (fixed or mobile, ground/water or air-based) base station 12; a mobile retroreflector 16; optical components 24 for a spectroscopic measurement; target tracking; and modeling. Included are the "center-pivot" or "hub-and-spoke" concept expressed above, as well as mapping and atmospheric modeling for dispersal.

In other embodiments, the present disclosure provides combinations with fixed reference reflectors and multiple wavelengths/pollutants/gases, as well as various types of spectroscopy (absorption, reflection; UV-visible, Near-Infrared (NIR), Mid-Infrared (MIR), Far-Infrared (FIR), Tetrahertz (THz), etc.).

In other embodiments, the present disclosure provides base stations 12 that are themselves mobile, i.e., on water, land, air or space. In other embodiments, the present disclosure provides point source monitoring such as stack gas emission modeling by transecting a smoke-stack, and also UAV-based estimates of gas flow rates at stacks, plus tools and techniques for wind direction and velocity measurements for gas monitoring. In other embodiments, the present disclosure provides various types of implementations (i.e., not just reflecting telescopes), various optical configurations and adaptations, specialized software for planning, remote charging stations.

In other embodiments, the present disclosure discusses using UAVs for construction to build remote base and charging stations, or serving as remote bases and charging stations, or that land to form semi-permanent fixed retroreflector stations.

In other embodiments, the present disclosure includes all of the above augmented with fixed retroreflector stations near known potential sources to serve as early warning monitors and for other purposes.

In other embodiments, the remote retroreflector 16 can be replaced with a detector, and the detected light signals sent back to the base station via a radio transponder (or some other means). The benefits of this are (1) substantially longer range since the range is limited by diffraction effects that depend on the size of an aperture, and large apertures are easier to have at the base station, (2) lower laser powers are needed at the same distance, improving safety and possible FAA limitations, and (3) eliminates the need for a very high quality retroreflector with a large aperture that could be heavier and more expensive than a detector.

Figure 3:
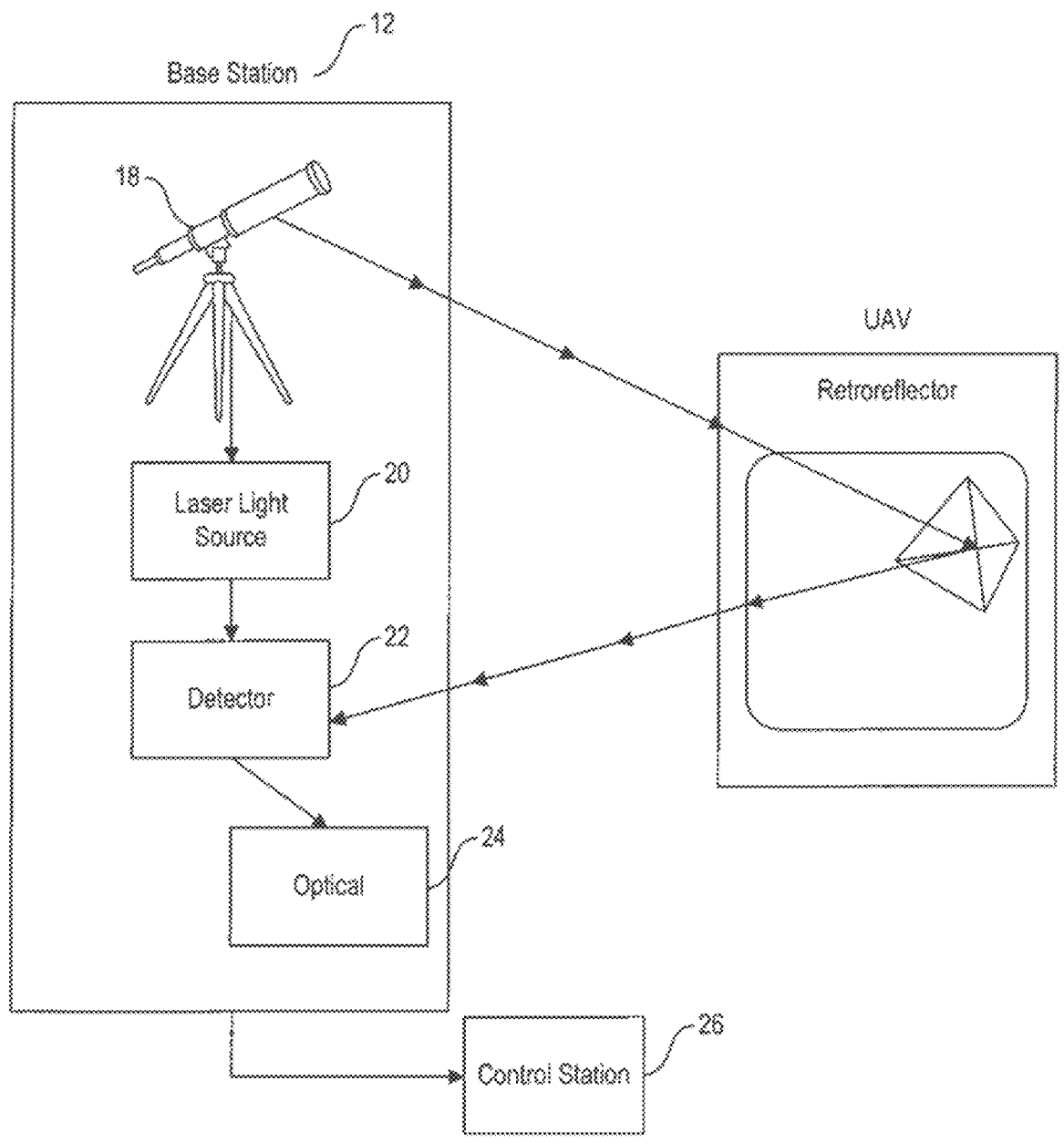
FIG. 3 illustrates an alternate embodiment of the spectroscopy system where a control station directs both the mobile retroreflector and the telescope within the base station.

In other embodiments, a control station 26, as shown in FIG. 3, can be in communication with base station 12. In one embodiment, control station 26 is coupled to telescope 18. Control station 26 can control telescope 18 and the exchange of light signals between telescope 18 and one or more mobile retroreflectors 16.

FIGS. 4-12 illustrate various use-based examples of spectroscopy system 10 utilizing various embodiments of the present disclosure. The use cases includes scenarios such as model validation implementation; rapid response; centralized community monitoring; and hazardous site alert-based monitoring.

Figure 4:
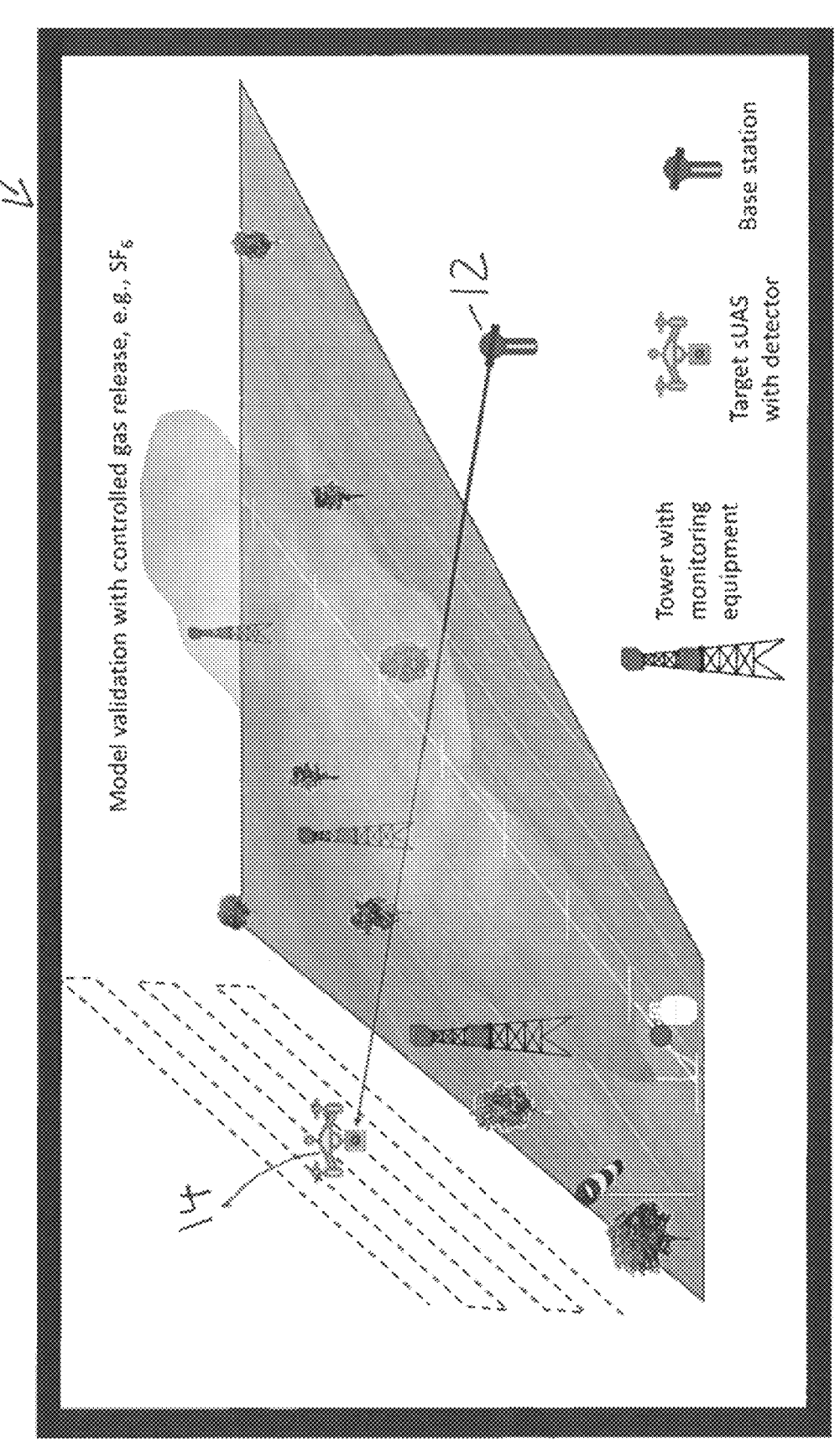
FIG. 4 illustrates an aerial view of a spectroscopy system in a testing/modeling scenario utilizing aspects of the present disclosure.

FIG. 4 illustrates an aerial view of spectroscopy system 10 in a testing/modeling scenario utilizing aspects of the present disclosure. In the embodiment illustrates in FIG. 4, a controlled release upwind is measured at a test site that has been instrumented with calibrated detectors (e.g., mass spectrometers, FTIRs, or other). Thus, in this scenario, the target sUAS 14 includes one or more detectors. In the event of an acute/spot release of a plume, the raster-scan of the plume can provide total release. But in a continuous release scenario, the release rate measurement depends on both the concentration observed, and also on the wind speed and whether this can be measured or estimated in real time.

Figure 5:
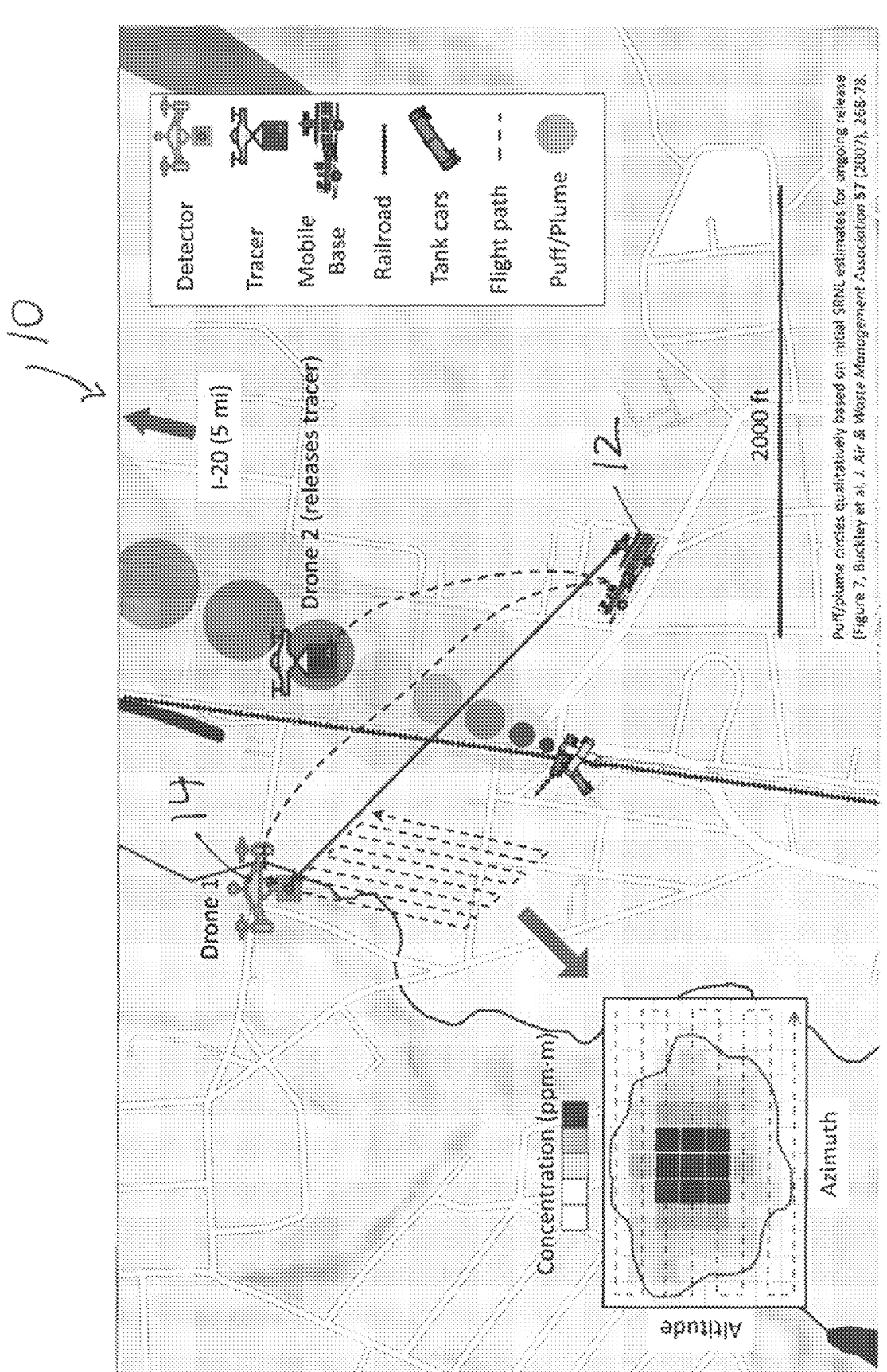
FIG. 5 illustrates an aerial view of a spectroscopy system in another testing/modeling scenario utilizing aspects of the present disclosure.

FIG. 5 illustrates an aerial view of spectroscopy system 10 in another testing/modeling scenario utilizing aspects of the present disclosure. The scenario depicted in FIG. 5 is based on an actual Cl2 (g) release of gas in a city. In this case, an emergency vehicle is equipped with one or more sUAS and optical systems for short-moderate distances (active optics not necessary; smaller apertures possible). FIG. 5 shows a detector on the sUAS 14. Measurements would be relayed by telemetry and limited signal processing would be done on the sUAS 14 before transmission to reduce the data transmission requirements. In one embodiment, sUAS 14 would be launched from the emergency vehicle. A tracer could be released into a plume to make visual or olfactory detection easier, or to simplify detection by other sensors. A raster-scan pattern of sensor measurements can be used to build a low-resolution image of the plume and to determine the total amount of gas released. The distance to and the orientation of the plume can be determined by flying toward and away from the emergency vehicle and observing the loss of signal along different azimuths.

For this scenario, IR light may not provide the optimal means of detection and visible light may be better due to the yellow-green color of chlorine gas. For most other gases, IR would be preferred for measurement. Note that in the actual incident, the amount of chlorine released was unknown. The next day it was determined that 40% of the chlorine in the breached railcar had not yet escaped through the "fist-sized" hole in the tank, which was likely due to the cold weather and evaporative cooling of the chlorine liquid. The hole was plugged with about 30 tons remaining in a 90 ton tank. It was noted in a report that if the hole had been in the bottom of the tank, the internal pressure would have forced all the chlorine out quickly, resulting in a very large release. In one embodiment, two different detectors can be utilized; one for IR and one for UV/Vis wavelengths, in order to handle all the lasers used at base station 12.

Figure 6:
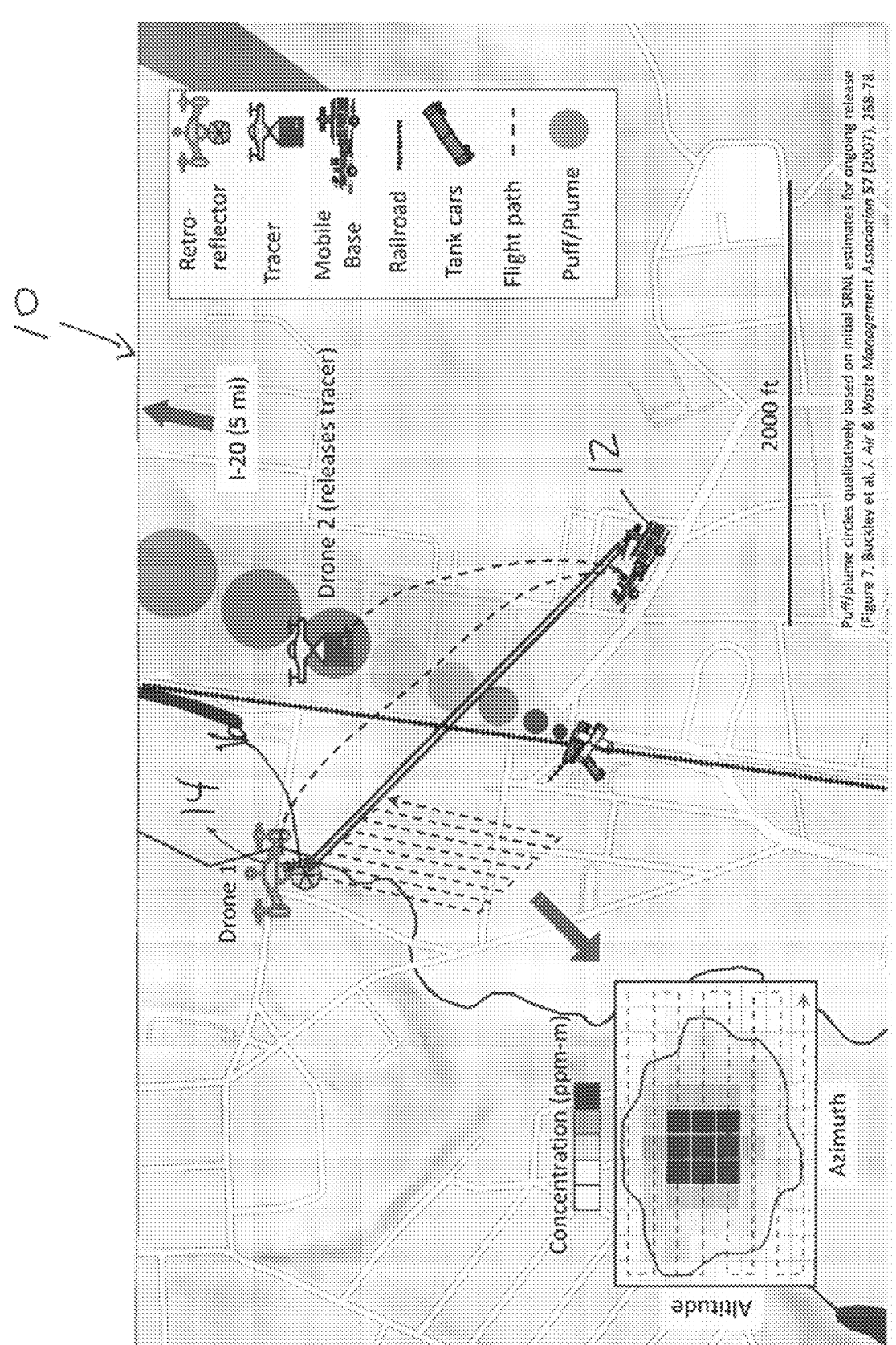
FIG. 6 illustrates the testing/modeling scenario of FIG. 5 including a retroreflector on the sUAS.

FIG. 6 illustrates the testing/modeling scenario of FIG. 5 including a retroreflector 16 on sUAS 14. The embodiment shown in FIG. 6 is the same as FIG. 5 except a retroreflector 16 is used on the sUAS 14. No signal processing is necessary on the sUASs 14. Note again that UV/V light is better for detecting Chlorine, while IR is better for other gases. For UV/Vis, one approach is to use two colors (e.g., blue and green or blue and red) that are rapidly chopped together to detect the broad-band absorption spectrum of chlorine vapor. QCLs are typically better for IR measurements of the narrow rotational structure of gases as Chlorine doesn't have any IR absorption. Possible interferences for visible laser for Chlorine are chlorophyll/pollen, which might mean adding another light source at 660 nm to specifically detect chlorophyll.

Figure 7:
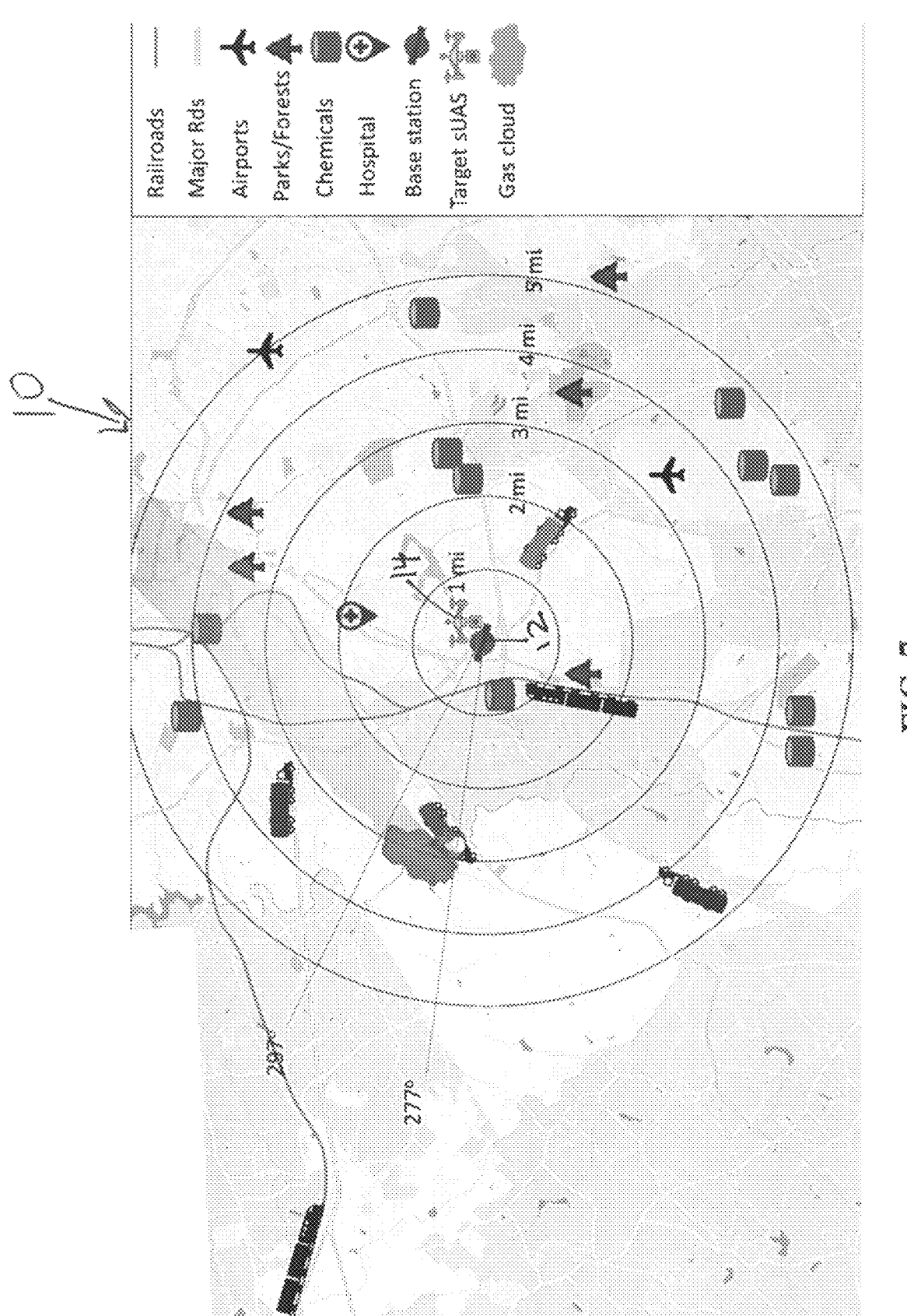
FIG. 7 illustrates an aerial view of yet another embodiment of the spectroscopy system of the present disclosure.

FIG. 7 illustrates an aerial view of yet another embodiment of the spectroscopy system 10 of the present disclosure. Base station 12 includes optical components 24 and is in communication with sUAS 14. System 10 is optimized for long distances (i.e., large apertures, good collimation, optimal tracking algorithms, and active optics. In one embodiment, sUAS 14 includes a detector. In the aerial view of FIG. 7, chemical plants, forests, airports, a hospital and major roads and railroads are illustrated. In the scenario depicted in FIG. 7, a tanker truck has been in a crash 3 miles from base station 12 at an azimuth between 277-297 degrees from the base station 12. The present and future locations of the plume can be seen.

Figure 8:
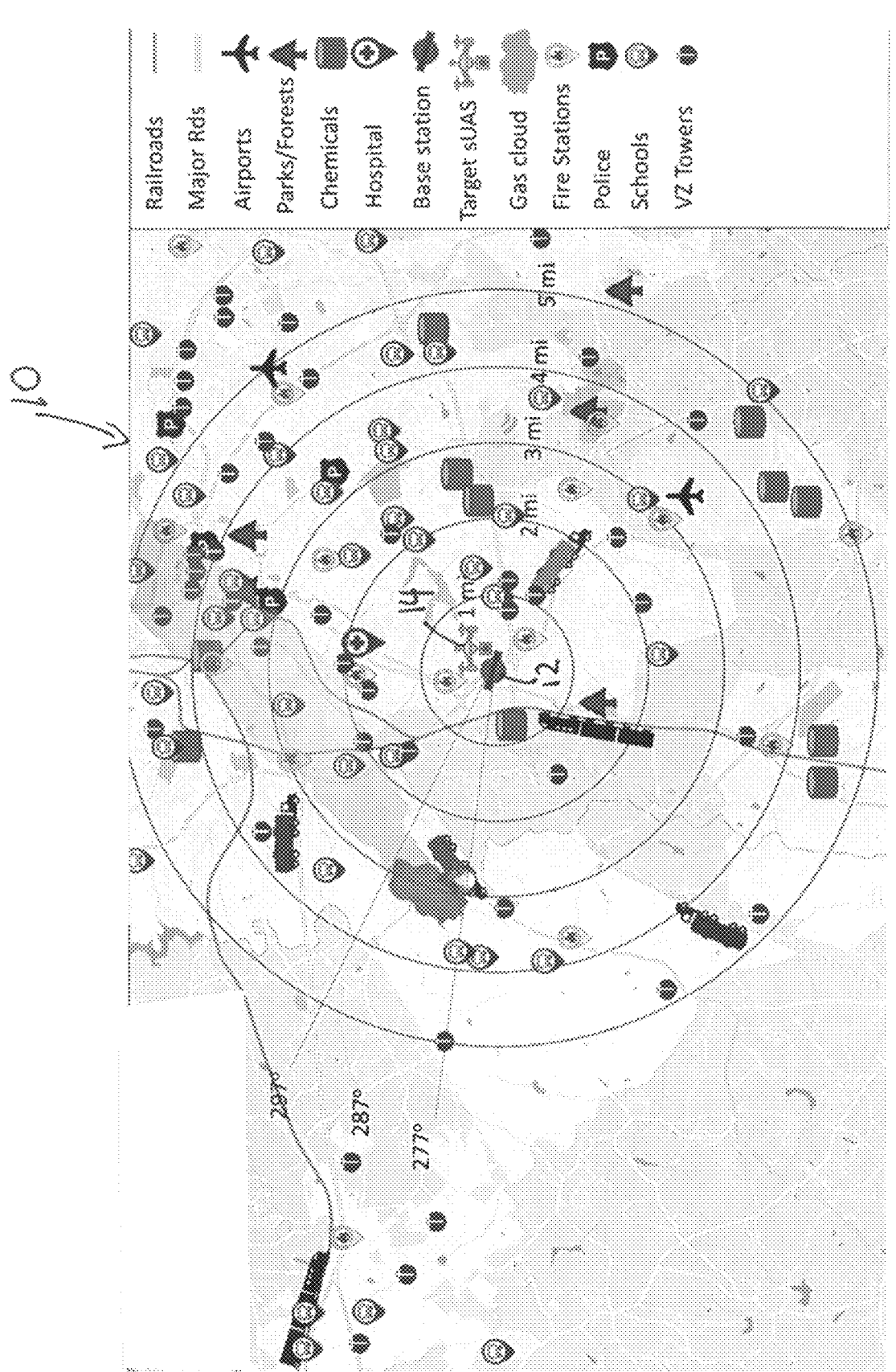
FIG. 8 illustrates the embodiment of FIG. 7 including various landmarks.

FIG. 8 illustrates the embodiment of FIG. 7 including various landmarks. In this scenario, schools, cell towers, police stations, fire stations, airports, and industrial chemical plants all provide high value public locations that could host a receiver or retroreflector 16, and most provide mainte- nance services to keep them operating. A central base station 12 can survey many locations quickly at all times of day or night. Only possible receiver locations near the plume azimuth are illustrated; there can be receivers scattered across the metropolitan area. In the scenario illustrated, a plume is detected by a receiver on a cell tower 6½ miles from base station 12. Two additional receivers are at a school and cell tower at 277 degrees azimuth from base station 12 and also detect the plume. Other nearby receivers at less than 277 degrees azimuth do not observe the plume. The pre- vailing winds are to the NW.

Figure 9:
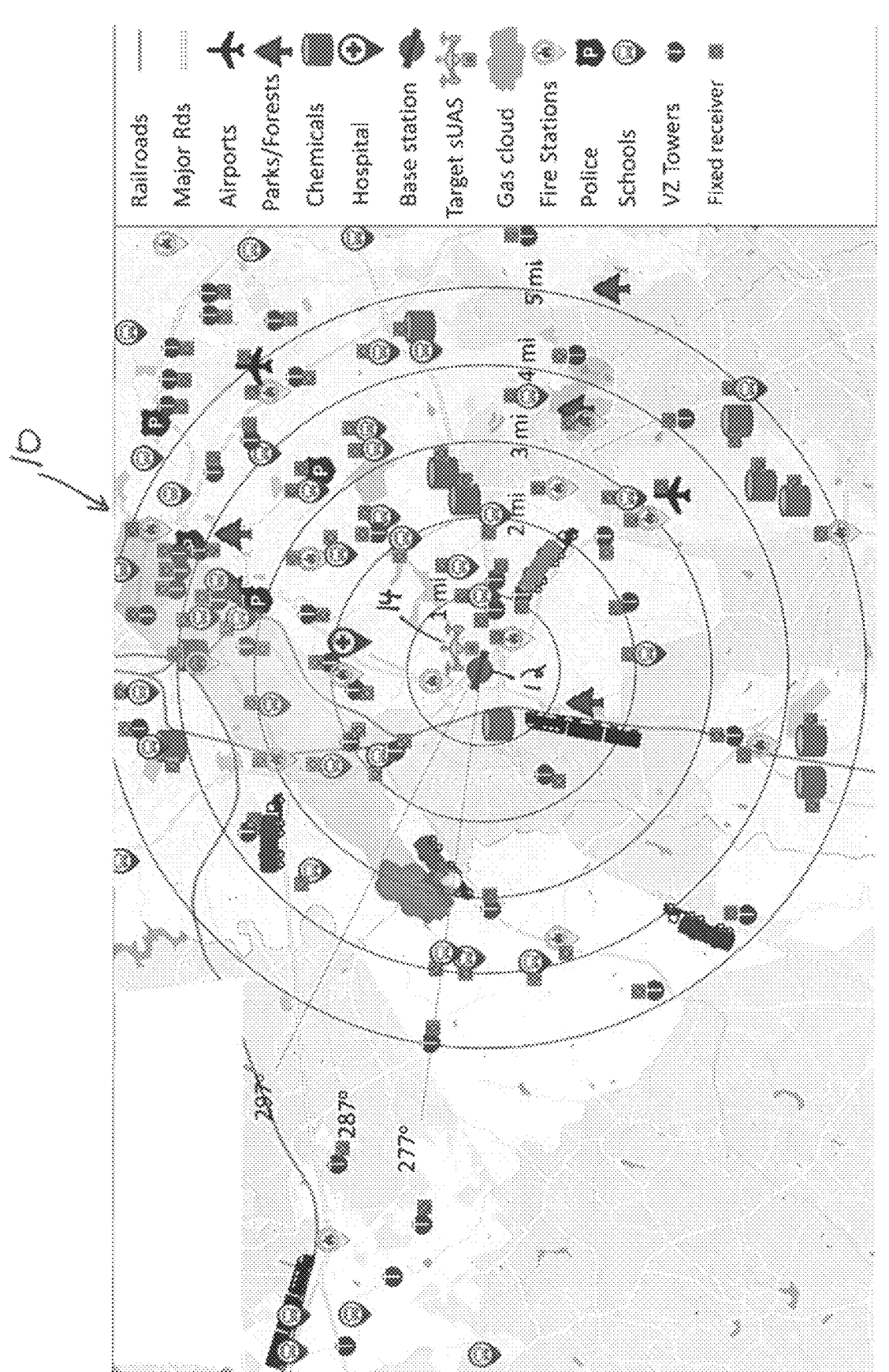
FIG. 9 illustrates the embodiment of FIG. 8 with additional landmarks.

FIG. 9 illustrates the embodiment of FIG. 8 with addi- tional landmarks.

Figure 10:
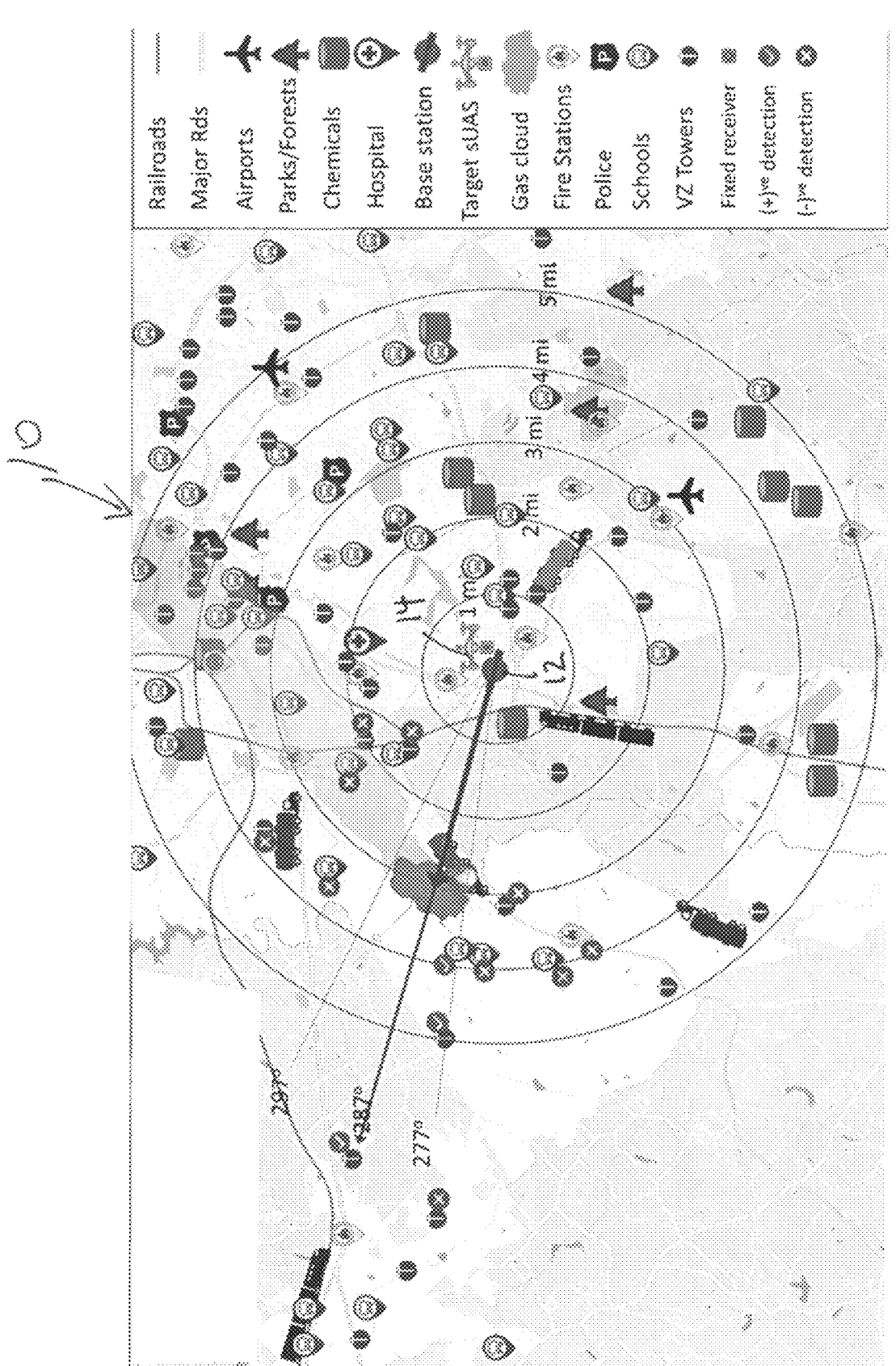
FIG. 10 illustrates an aerial view of yet another embodiment of the spectroscopy system of the present disclosure.

FIG. 10 illustrates an aerial view of yet another embodi- ment of the spectroscopy system 10 of the present disclo- sure. In the scenario illustrated in FIG. 10, a plume is detected by a receiver on a cell tower 6½ miles from base station 12. Two additional receivers are at a school and cell tower at 277 degrees azimuth from base station 12 and also detect the plume. Other nearby receivers at less than 277 degrees azimuth do not observe the plume. The prevailing winds are to the NW.

Figure 11:
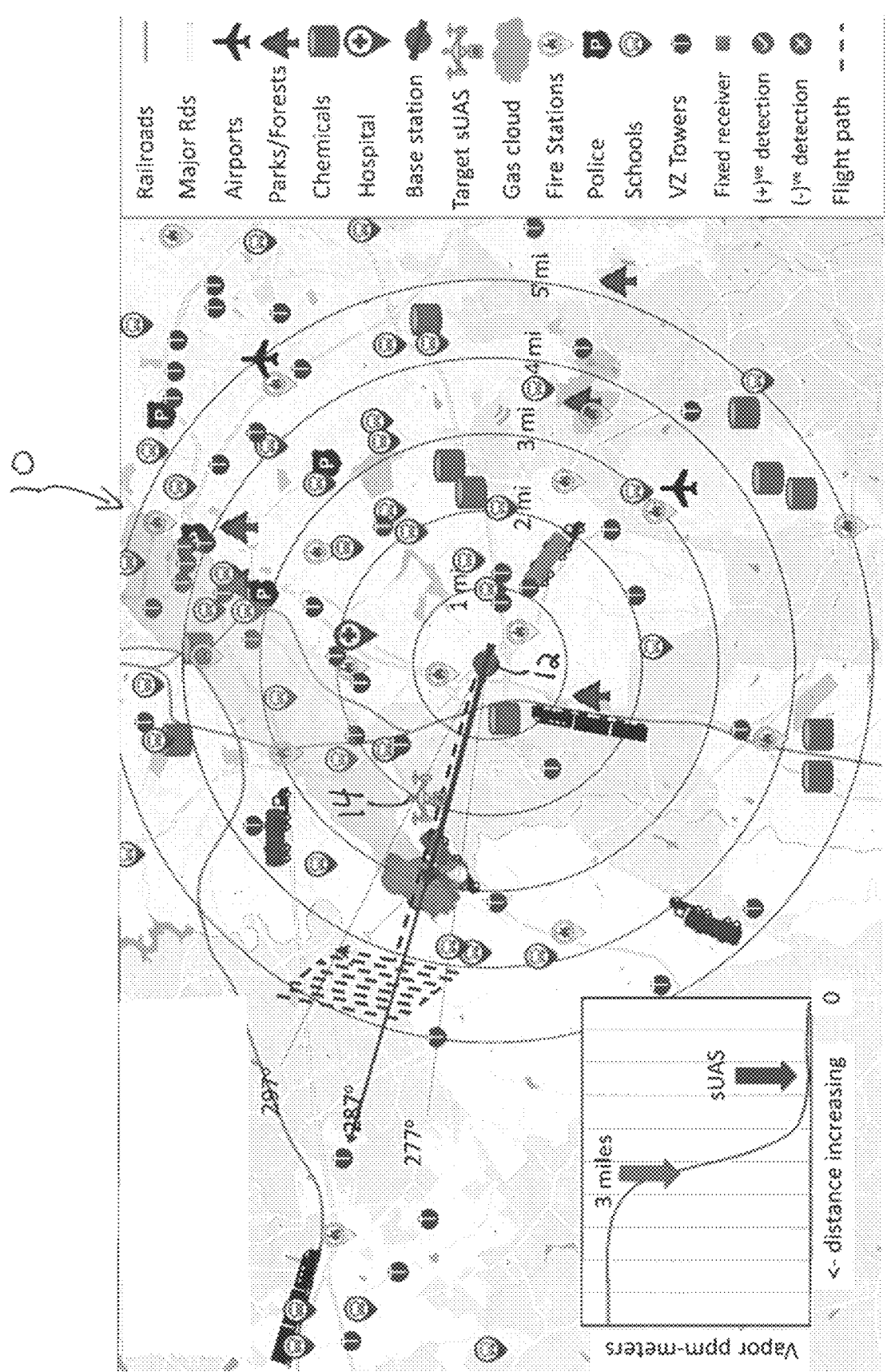
FIG. 11 illustrates an alternate aerial view of the spectroscopy system of the present disclosure where an sUAS is launched from the base station area and flies directly towards a detecting station.

FIG. 11 illustrates another aerial view of spectroscopy system 10. In this non-limiting embodiment, a sUAS 14 is launched from base station 12 and flies directly toward one of the detecting stations. At its present position 1.5 miles from base station 12, no absorbance due to the plume is detected. As sUAS 14 flies further, it passes through the plume center at 3 miles and the absorption due to the vapors increases. The highest concentration of the plume is where the rate of increase of absorption with distance is greatest. The sUAS 14 can then fly in a pattern behind the plume to define its edges and can adjust the flight pattern to follow the plume as it disperses. Additional sUASs 14 can be sent in response, including, e.g., tracer and camera systems.

Figure 12:
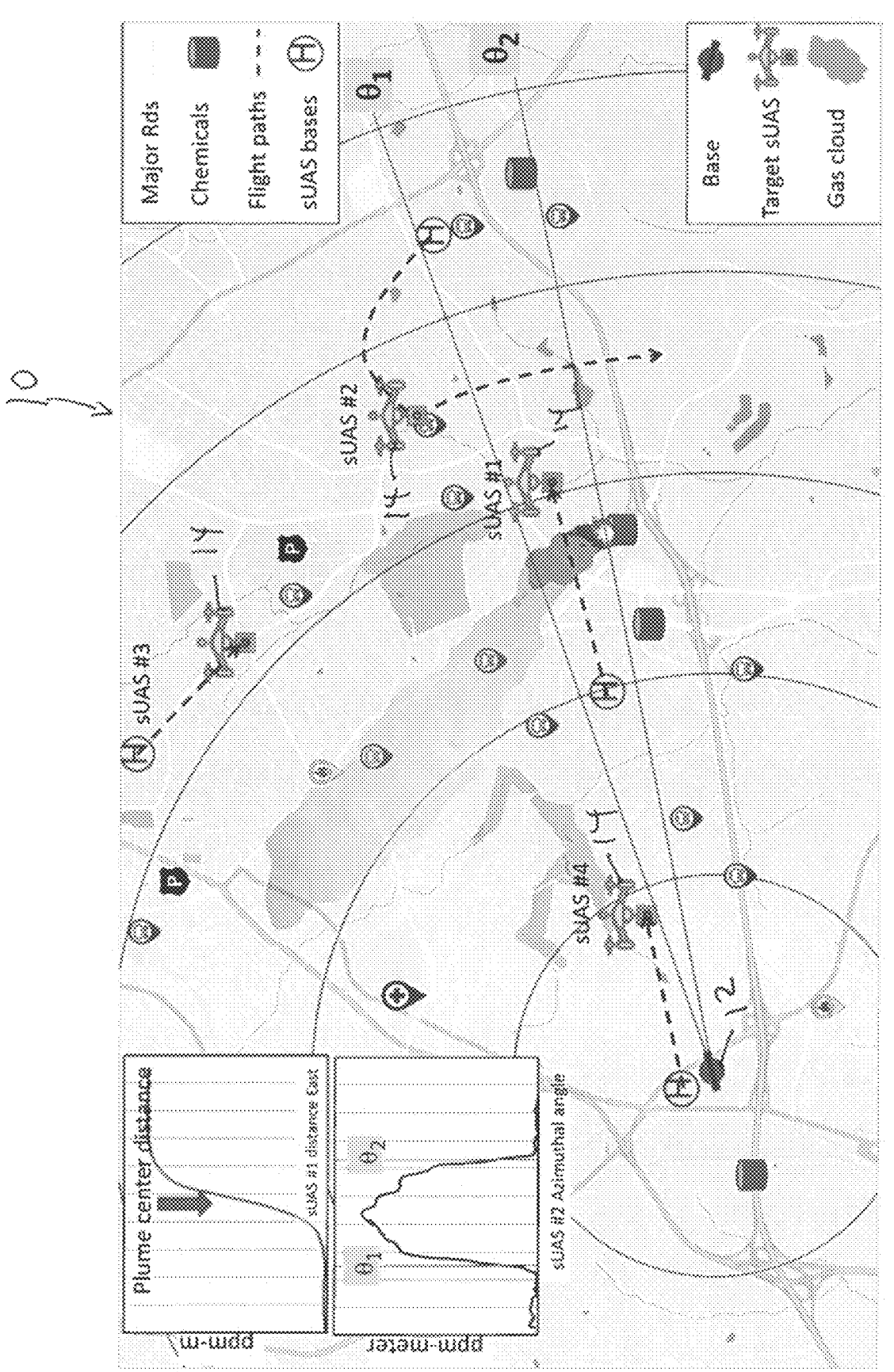
FIG. 12 illustrates an aerial view of the spectroscopy system of the present disclosure where a series of sUAS bases provide response to an alarm.

FIG. 12 illustrates an aerial view of the spectroscopy system 10 of the present disclosure where a series of sUAS 14 provide response to an alarm. In this community-based scenario, a series of sUAS bases 14 provide rapid response to an alarm at a predefined site. Multiple sUAS 14 can respond. In the scenario shown, sUAS #1 is the closest responder and flies over the site with a camera and detector. sUAS #2 flies behind the plume to map its boundaries. sUAS #1 and #2 continue to explore the plume while the densest part of the plume as determined by sUAS #1. sUAS #3 and sUAS #4 cycle in to the response to maintain continuous coverage while sUAS #1 and sUAS #2 return to the nearest base for charging. sUAS #3 sUAS #4 end their missions at the nearest base to the emergency for recharge or exchange of batteries so they can return most quickly and maintain coverage for a multiple hour event. At the end, sUASs 14 return to their own stations. Base stations 12 can be placed at the center of mass of sites rather than the "center of town."

In other embodiments, the present disclosure includes any software for preflight planning and execution, and for inci- dent response and mapping. In other embodiments, the present disclosure includes, in combination with the above: any optical or physical sensors deployed from UAVs; spot- ting UAVs used to confirm conditions on the ground where the retroreflector or base station are deployed, as well as autonomous or triggered sample collectors for water/air/soil/ plant material.

In other embodiments, the present disclosure includes mirror devices other than retroreflectors, such as (but not limited to) 90-degree reflectors to direct light toward the ground or elsewhere plus laser pyrolysis combined with mass spectrometry, spotter UAVs and planning software, etc.

Among the types of spectroscopy are implicitly disclosed herein among those described above: frequency comb spec- troscopy, dual frequency comb spectroscopy, multivariate optical computing, and in general any type of measurement in which light is transmitted from any kind of base station to a UAV for the purpose of powering the UAV or a measure- ment on the UAV, or being directed back to the source, or being reflected to a sample, in place of a light source directly on the UAV. This should be generalized to any type of retroreflector, mirror, refractive optic, reflective optic, dis- persive optic, or prism device carried by the UAV. It should also be generalized to any application, like terrestrial vapor monitoring, stack gas measurement, area survey, leak detec- tion, planetary science (e.g., there's a laser- and detector- carrying rover on Mars right now with a small UAV suffi- cient to carry a retroreflector), and other applications as a person skilled in the art might reasonably foresee.

Base stations, as defined here, provide support for the major instrumentation used for measurements—lasers, tele- scopes, tracking electronics and motors, guidance, comput- ers, etc.—so that they don't need to be contained on the remote UAV. In some embodiments, base stations can include an extensible lift, boom, or tower, or can be based on a tower, or on top of a building or antenna, to elevate the base station above low obstacles.

While the present subject matter has been described in detail with respect to specific exemplary embodiments and methods thereof, it will be appreciated that those skilled in the art, upon attaining an understanding of the foregoing may readily produce alterations to, variations of, and equiva- lents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art using the teachings disclosed herein.

What is claimed is:

1. A spectroscopy system comprising:
   a base station comprising:
      a reflecting telescope and a laser light source coupled to the telescope, the laser providing an outgoing light signal;
      a detector to record intensity of a returning light signal; and
      optical components for spectroscopic measurements, the optical components utilizing the intensity of the returning light signal, revealing the presence of a chosen narrow band for the purpose of detecting a target;
   at least one Unmanned Aerial Vehicle (UAV) containing at least one optical detector configured to receive the light signal from the laser and return the light signal back to the telescope via at least one radio transponder to increase range of the UAV; and
   at least one sensor configured to form a raster-scan pattern of sensor measurements to build at least one low- resolution image of a gas plume to determine a total volume of gas release by the gas plume and to compute an amount of material released with the gas plume as well as to predict downwind exposure from the amount of material released by the gas plume.

2. The spectroscopy system of claim 1, wherein the laser light source is a quantum cascade laser (QCL).

3. The system of claim 2, wherein the detector is configured to sweep the returning light signal in wavelength to reveal the presence of the chosen narrow band to detect a target compound in a atmosphere.

4. The system of claim 1, wherein the base station further comprises at least one actuator to allow the telescope to track a path of the mobile retroreflector.

5. The system of claim 1, wherein the base station is fixed.

6. They system of claim 1, wherein the base station is mobile.

7. The system of claim 1, wherein the base station is at least one of ground-based, water-based, or air-based.

8. The system of claim 1, wherein the detected target is one or more gases.

9. The system of claim 1, wherein the detector and the optical components are located in the base station.

10. The system of claim 1, further comprising at least one of a beacon and a fiduciary mark located on or near the at least one mobile retroreflector, wherein the telescope is configured to track the at least one mobile retroreflector by following the beacon or fiduciary mark.

11. The system of claim 1, wherein the telescope is configure to track the at least one mobile retroreflector by using a Global Navigation Satellite System (GNSS) Real Time Kinematic (RTK)-derived position/heading broadcast received from the at least one mobile retroreflector.

12. The system of claim 1, further comprising a control station coupled to the telescope, the control station configured to direct the at least one mobile retroreflector and the telescope in order to coordinate tracking of the at least one mobile retroreflector by the telescope.

13. They system of claim 1, wherein the UAV has a preprogrammed circular flight path.

14. The system of claim 1, further comprising fixed retroreflector stations near known potential sources.

15. The system of claim 1, where the UAV further includes one or more mirrors, refractive optics, reflective optics, dispersive optics, and prism device.

16. The system of claim 1, wherein the base station and components therein are configured for at least one of terrestrial vapor monitoring, stack gas measurement, area survey, leak detection, and planetary science.

\* \* \* \* \*